United States Patent [19]
Kildal et al.

[11] Patent Number: 5,507,388
[45] Date of Patent: Apr. 16, 1996

[54] CARTRIDGE-FREE STACKS OF SLIDE ELEMENTS

[75] Inventors: Maurice A. Kildal, Webster, N.Y.; Frank A. Richardson, Charlotte, N.C.; Claude E. Monsees, Fort Mill, S.C.

[73] Assignee: Johnson & Johnson Clinical Diagnostics, Inc., Rochester, N.Y.

[21] Appl. No.: 317,972

[22] Filed: Oct. 4, 1994

Related U.S. Application Data

[62] Division of Ser. No. 37,176, Mar. 26, 1993, Pat. No. 5,384,947, which is a continuation of Ser. No. 810,229, Dec. 19, 1991, abandoned.

[51] Int. Cl.⁶ ............................................. B65D 85/00
[52] U.S. Cl. ................. 206/459.5; 206/456; 206/526
[58] Field of Search .................................. 206/340, 345, 206/346, 459.5, 456, 526

[56] References Cited

U.S. PATENT DOCUMENTS

| | | | |
|---|---|---|---|
| 3,802,987 | 4/1974 | Noll | 206/345 |
| 4,187,077 | 2/1980 | Covington et al. | |
| 4,190,420 | 2/1980 | Covington et al. | |
| 4,359,157 | 11/1982 | Horstmann | 206/459.5 |
| 4,377,890 | 5/1983 | Miller | |
| 4,440,301 | 4/1984 | Intengan | |
| 4,482,521 | 11/1984 | Bunce et al. | |
| 4,621,732 | 11/1986 | Olson | 206/346 |
| 4,662,974 | 5/1987 | Roberts | |
| 4,805,772 | 2/1989 | Shaw et al. | 206/459.5 |
| 4,811,861 | 3/1989 | Roberts | |
| 4,850,488 | 7/1989 | Humbert | 206/459.5 |
| 5,081,038 | 1/1992 | Sugaya et al. | |
| 5,384,947 | 1/1995 | Kildal et al. | |

FOREIGN PATENT DOCUMENTS 952811  5/1949  France ........................... 206/459

*Primary Examiner*—David T. Fidei
*Attorney, Agent, or Firm*—Dana M. Schmidt

[57] ABSTRACT

A stack of plastic articles and a process of forming the stack are disclosed. Preferably the stack is of heat-fusible plastic slide elements for use in a diagnostic analyzer, the elements being temporarily and non-destructively fused together so that the stack can be used free of a cartridge.

In another embodiment, the stack can be of any plastic article temporarily fused to adjacent elements, one side edge of each element bearing a colorant and another bearing no colorant, so that a bar code for the stack is inherently formed simply by rotating each element to project outwardly the colored side edge or the side edge lacking colorant, prior to fusing the elements together.

4 Claims, 4 Drawing Sheets

CARTRIDGE-FREE STACKS OF SLIDE ELEMENTS

This is a divisional of application Ser. No. 08/037,176, filed Mar. 26, 1993, now U.S. Pat. No. 5,384,947 which is a continuation of application Ser. No. 07/810,229, filed Dec. 19, 1991, now abandoned.

FIELD OF THE INVENTION

This invention relates to a stack of slide-like test elements used in a diagnostic analyzer, and particularly aspects allowing the stack to be so used, free of any cartridge.

BACKGROUND OF THE INVENTION

In the field of dry slide diagnostic analysis, it has been most common, particularly in the large analyzers, to package the slide test elements in a cartridge. Such cartridges keep the essentially identical members of a particular lot of an assay together, and allow the analyzer to properly interface with the slide elements. These features are illustrated in, e.g., U.S. Pat. Nos. 4,187,077 and 4,190,420.

Notwithstanding the outstanding success of such packaging, as witnessed by the hundreds of thousands of cartridges that have been sold in the 80's by Eastman Kodak Co. under the trademark "Ektachem", there remains some drawbacks in such use of cartridges. That is, the cartridges are a sizable contribution to the expense of the slide elements, and further require a careful determination of when they are empty, as is explained in the aforesaid '420 patent. Still further, even after determining that they are empty, the empties have to be disposed of—a sizable problem as throughput is increased. Because of these drawbacks, there has been interest in packaging an assembly of slide elements without requiring the use of a cartridge. However, due to the fact that the readily apparent solutions lack a sturdy way of keeping together the identical, lot-specific members of the stack, sans cartridge, there has not been an acceptable way of eliminating the cartridge prior to this invention.

Yet another drawback of cartridge-supplied slide elements has been the manner in which coded information is supplied to identify the assay of the cartridge, e.g., by bar codes. Either the cartridges are printed directly, or printed labels have been used heretofore. Such labels require a separate printing operation and then a correct combining of the printed label with its associated cartridge. It would be more advantageous to inherently provide the coding, e.g., a bar code, simply by the act of assembling together the stack of slide elements.

SUMMARY OF THE INVENTION

We have designed an assembly of slide elements that solves the above-noted problems.

More specifically, the invention in one aspect provides an assembly of slide-like test elements suitable for insertion into a diagnostic analyzer, the assembly comprising a plurality of slide-like elements placed one on another to define a stack having at least one side face, each of the test elements comprising a heat-fusible plastic frame and at least one reagent within the frame capable of producing, in response to the presence of an analyte, a detectable signal; each of the frames of the stack being temporarily fused to the next adjacent frames.

In another aspect of the invention, there is provided a stack of slide-like elements assembled together, the stack comprising heat-fusible plastic frames of generally planar configuration, disposed in the stack one above another, the stack having at least one side face, means for temporarily holding the frames together at least a common side edge of the frames, and a bar-code extending along the at least one side face of the stack.

In still another aspect of the invention, there is provided a method of affixing together a group of completed slide-like test elements for use in an analyzer, comprising the steps of:

a) assembling together into a stack, one above the other, a plurality of slide-like test elements each of which comprises a heat-fusible plastic frame and at least one reagent effective to test a patient liquid in an analyzer, to form at least one stack side face, b) temporarily heat-fusing the elements together as a stack by fusing at least a portion of at least one side edge of the frame of each element to the side edge of the frame of an adjacent element along the at least one side face of the stack, and c) inserting the stack of temporarily fused test elements into an analyzer.

In yet another aspect of the invention, there is provided a method of encoding in colored and white bars a stack of articles each having at least two side edges, one of which is totally white and the other of which has a portion bearing an exposed colorant, the method comprising a) assigning some of the elements of the stack the value of the colored part of a colored and white bar code, and b) assembling in proper sequence the stack so that the assigned some elements have the colored side edge showing and the rest of the stack elements have the white edge showing, in the sequence of the colored and white code.

Still another aspect of the invention features a temporary stack of plastic articles individually releasable from the stack, and bearing bar coded information, the stack comprising a plurality of individual plastic articles each comprising at least two exposable side edges, one of the edges having an exposed colorant in at least a portion of its surface and the other of the edges being substantially free of colorant, the articles being temporarily fused to each other so that the one side edges bearing the exposed colorant are placed in the stack with the other, colorless side edges so as to inherently form the bar-coded information by the colored edges alternating with the colorless edges in the sequence of said coded information.

Accordingly, it is an advantageous feature of the invention that an assembly of slide elements is provided for storage and use in an analyzer as an entire stack, without necessitating the added complicating presence of a cartridge.

It is another advantageous feature of the invention that necessary codes can be provided simply by the manner in which the slide elements are assembled in such a stack, avoiding the need for printing and attaching a coded label.

Other advantageous features will become present upon reference to the following Detailed Description, when read in light of the attached drawings.

DESCRIPTION OF THE PREFERRED EMBODIMENTS

The invention is described in connection with the certain preferred embodiments, in which the slide elements of the stack are primarily those heretofore described in the patent literature and available under the registered trademark "Ektachem" from Eastman Kodak Company. In addition, the invention is useful with any slide element comprising a frame of heat-fusible plastic of any kind, regardless of how it is otherwise constructed, or assembled, and regardless of whether it is conventional or not. That is, the invention is in the stack of slide elements useful in a diagnostic analyzer, and method of constructing and using such a stack, and not in the details or the assembly of the slide element construction per se. Still further, respecting the bar code portion of the invention, that portion is applicable to any plastic article that is bar coded, whether it is a slide element or not.

Figure 1:
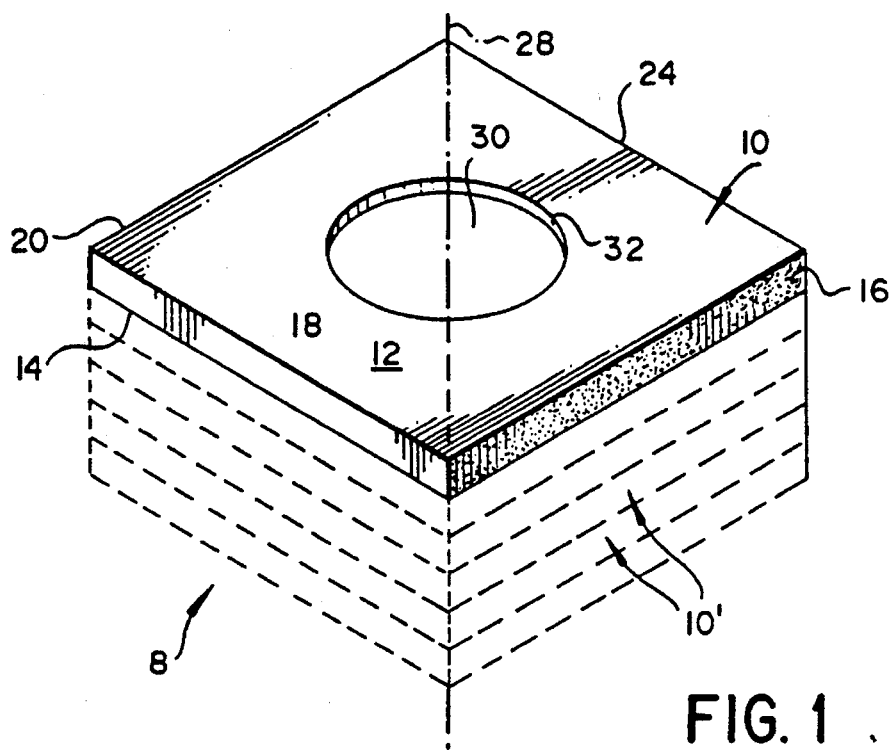
FIG. 1 is an isometric view of a slide useful in the process, and also of the stack of the invention, the stack being suggested in phantom.

Thus, as shown in FIG. 1, slide-like test elements particularly useful in the invention can be selected from any of the, e.g., colorimetric slide test elements 10 sold by Eastman Kodak Co. under the "Ektachem" trademark. These comprise, as is conventional, a heat-fusible plastic frame of polystyrene, surrounding and holding within the frame a reaction member of one or more layers 30, containing one or more reagents to provide a detectable change indicative of the amount of analyte present, when patient sample is added, as is well-known. Likewise, the invention is useful if the test element 10 is instead an ion-selective electrode test element (not shown) that also has a heat-fusible plastic frame made from polystyrene. In such an element, the reagent that is used to produce a detectable change includes, e.g., an ionophore that is selective for the analyte of choice, and the detectable change is an electric signal registered by the electrode (not shown). Again, such test elements are well-known under the registered trademark "Ektachem".

In accordance with one aspect of the invention, slide element 10 and all the others 10' shown in phantom, FIG. 1, can be affixed together in a stack which is useful in an analyzer without the need for a cartridge. Each of the elements 10, 10' has opposite major surfaces 12, 14, and side edges 16, 18, 20, 24, there being four such side edges in the preferred rectangular configuration. They are stacked so that the generally planar slide elements 10, 10' have their major surfaces 12, 14 in contact with the corresponding major surfaces 12, 14 of the next adjacent slide element. Most preferably, the stack has the side edges positioned so as to be coplanar, thus forcing an axis of symmetry 28 of the stack, to be generally perpendicular to each slide element.

Optionally, at least one but less than all of the side edges 16–24, for example edge 16, is coated with an exposed colorant, preferably a black colorant, such as a black pigment coated onto the plastic. Such colorant can cover all of the side edge, as shown, or only a portion thereof. The remaining side edges are left colorless or white. Its use is discussed hereinafter. As used herein, "colorant" refers to a color other than white.

As noted above, such slide elements, when ready for use in an analyzer as shown, include in an interior portion thereof, at least one layer 30 containing a reagent that produces a signal in response to an analyte. For colorimetric slide elements as shown, the reagent produces a change in density. A depositing aperture 32 is present in surface 12 of element 10, 10' to allow liquid to be deposited, and a viewing aperture (not shown) is formed in opposite surface 14, generally aligned with aperture 32 but not necessarily of the same size.

Figure 2:
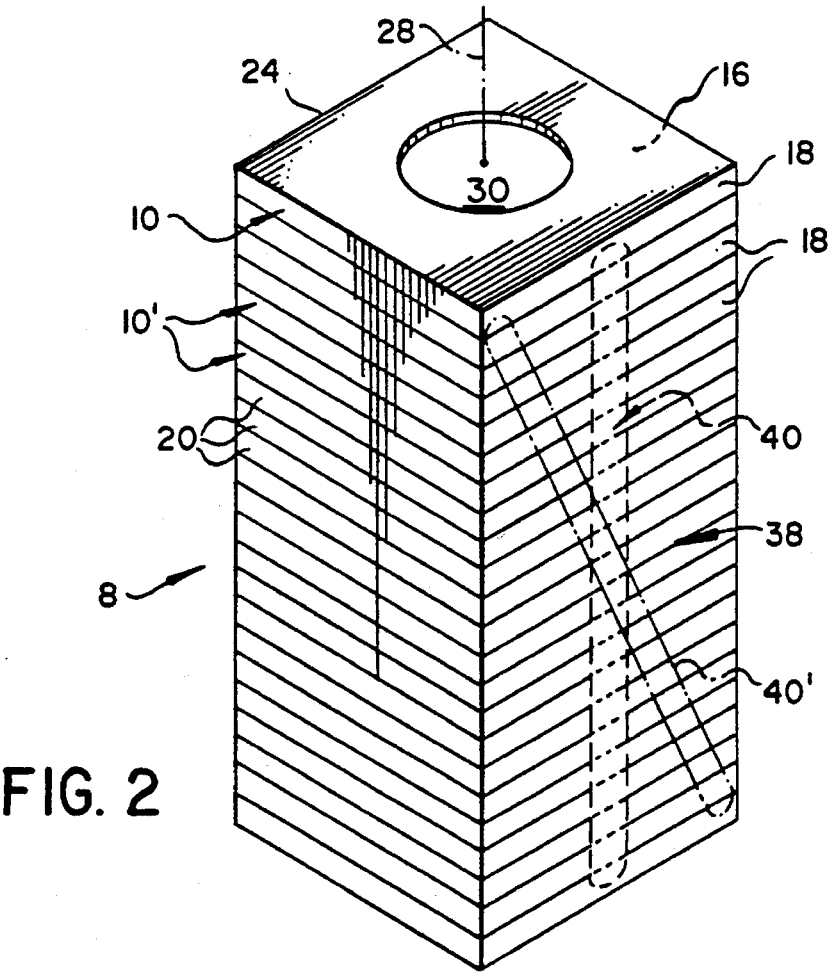
FIG. 2 is an isometric view of the completed stack, as it is shipped and stored in an analyzer.

In accordance with one aspect of the invention, the stack 8 of FIG. 1 is rendered usable in a diagnostic analyzer by temporarily fusing, FIG. 2, at least one of the common side edges of the elements 10, 10' in the stack, at a stripe 40 which necessarily extends the length of the stack to temporarily join all the elements together. As shown, stripe 40 occurs along each of side edges 18 of the slide elements, that is, each element 10, 10' has been oriented to align side edges 18 together, etc. to form a stack side face 38. Stripe 40 can occupy only a small portion of side edges 18, as shown, or a majority or all of that edge. Most preferably, it extends generally parallel to axis 28, but it will be readily obvious that it can be tilted at any angle, e.g., as shown in phantom, 40'. Only one such stripe is needed, but additional stripes can be used. Optionally, more than one side edge, e.g., side edges 20, can also be striped (not shown).

The striping phenomenon is more specifically described hereinafter. It is however a very slight fusion of the edges of the surface of the side edge so as to create no significant change in the geometry of the side edge. As used herein, "no significant change" means that when individual elements are shucked off the stack, it is difficult for the naked eye to detect any surface alteration where the stripe had been. Thus, the stripe, while holding the stack together temporarily, is not such a strong fusion that each slide element cannot be non-destructively sheared off the stack as described below. The fusion or striping process is that described in U.S. Pat. Nos. 4,662,974 and 4,811,861, to which attention is directed for further details.

Any plastic polymer is useful for the frames of the slide test elements (or whatever article is being stacked), provided it is heat-fusible to allow two test elements stacked together, to be temporarily heat-fused together at a side edge. Useful plastic polymers include thermoplastic polymers such as polyolefins and copolymers of olefins. Highly preferred are polystyrene, polyethylene, polypropylene, and the latter copolymerized with ethylene vinyl acetate.

Figure 3:
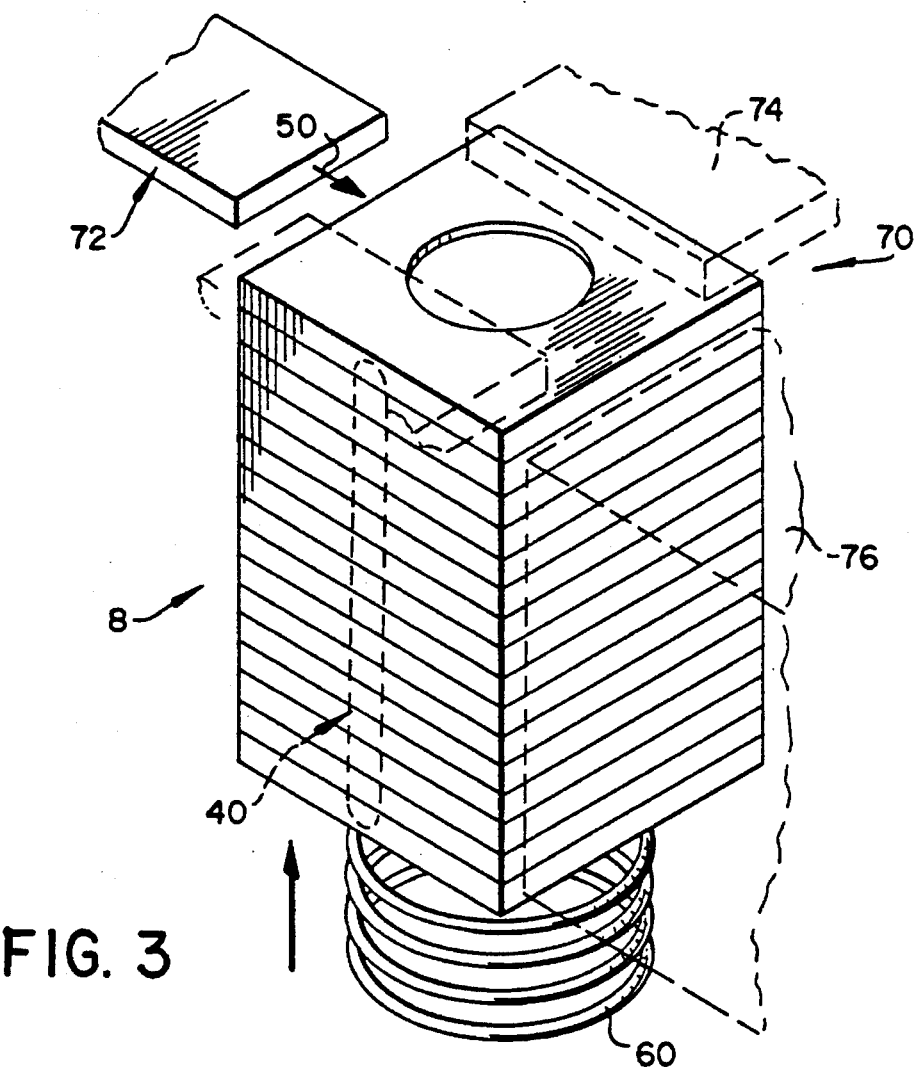
FIG. 3 is an isometric and slightly schematic, partially fragmented view of a storage and dispense station in an analyzer, using a stack in accordance with the invention.

As shown in FIGS. 2 and 3, "shucking" or shearing off of individual elements is achieved by applying a force 50 against one of the side edges of the element. Most preferably, it is applied to the side edge perpendicular to the side edge having the stripe, e.g., side edge 16, and in a direction generally perpendicular to axis 28. Because adhesion at stripe 40 is minimal, the shear force required is minimal, e.g., about 1 to 3 kg of force applied to a slide element side edge 24 having a surface area of about 15 mm$^2$ for polyethylene elements. Polystyrene elements require a higher force.

FIG. 3, when stack 8 is placed into an analyzer, it is preferably done so without benefit of a cartridge (and hence without the disadvantages of a cartridge). A biasing means, e.g. a spring 60, is used to urge the stack to a slide element dispersing station 70, which comprises means for applying force 50 against the top-most element 10 in the stack, e.g. a pusher blade 72, and a removable holding plate 74 for holding down the stack. (Plate 74 is shown for clarity as not covering completely top element 10, but it can also completely cover it.) Plate 74 is removable to allow stack 8 to be inserted. Additionally, station 70 includes a side support 76 abutting side face 78 of the stack. In this embodiment, stripe 40 is shown as being parallel to force 50 being applied for dispensing, but it can also be opposite to force 50 as shown in FIG. 2.

Figure 4:
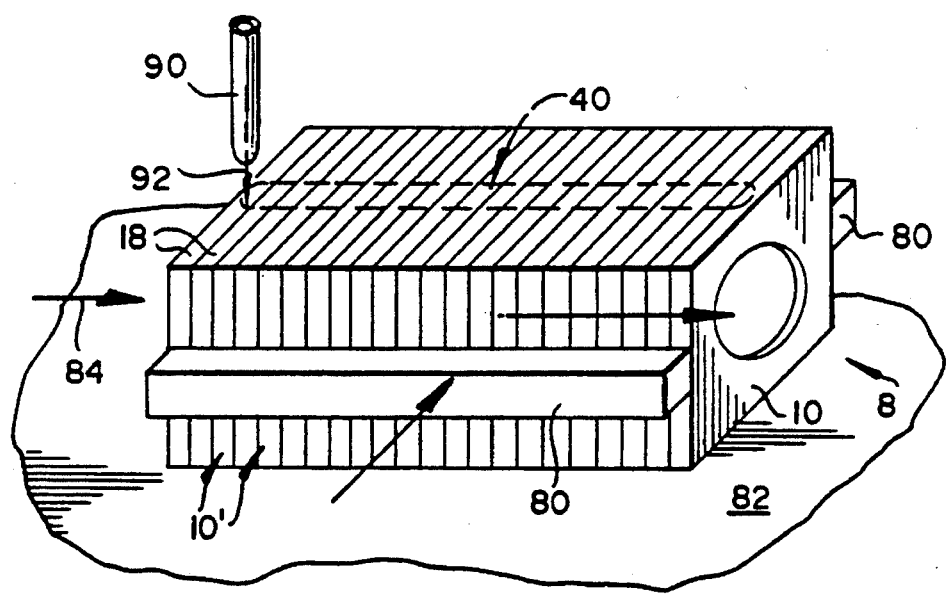
FIG. 4 is a fragmentary isometric view of a stack showing the process by which the elements thereof are temporarily fused together.

Stripe 40 is preferably formed, as mentioned above, by the technique of the aforesaid '974 and '861 patents. More specifically, in one useful method as shown in FIG. 4, slide elements 10, 10' are moved through guideways 80 on a surface 82, the guideways being applied with pressure to hold the assembled stack together. Surface 82 can be horizontal, vertical or tilted. The side edges to be striped, e.g. edges 18, are forced upwardly as elements 10 and 10' are faced, arrow 84, to advance between guideways 80. As the stack 8 advances, an air gun 90 projects a jet 92 of very hot air onto side edges 18, and the fusion stripe 40 is formed. The temperature of this jet is adjusted, depending upon the plastic that is being used. For example, if the frames of elements 10, 10' are polyethylene or polystyrene, the temperature is about 200°–215° C. The presence of the jet can be varied, and a useful pressure is about 50 cm of water.

Any number of elements 10, 10' can be so fused together to form stack 8. This is an improvement over analyzers requiring the use of a cartridge, since a cartridge is limited in its capacity.

Optionally (not shown), a blank element can be used as the top-most and the bottom-most element in each stack, which blank element comprises a solid frame without any apertures and without a reaction member within the frame. Such blanks at the ends provide useful protection against light exposure and/or physical damage to the reaction members of the test elements.

Figure 5:
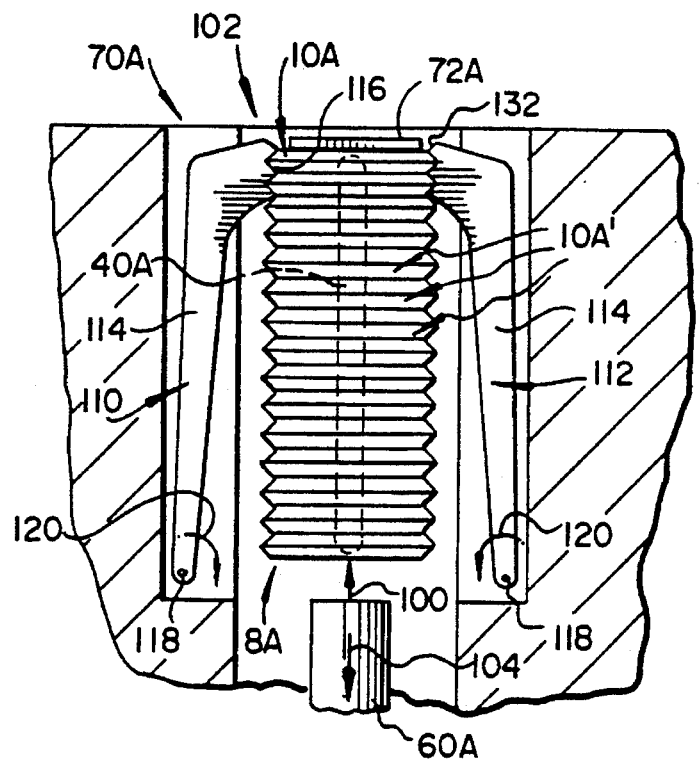
FIG. 5 is a fragmentary elevational view in section illustrating an alternative interface between the storage and dispensing station of an analyzer, and the assembled stack of the invention.

It is not necessary that a removable holding plate be used to hold the stack in place for dispensing. Instead, FIGS. 5 and 6, other mechanisms can be used. Parts similar to those previously described bear the same reference numeral to which the distinguishing suffix "A" is appended. Thus, FIG. 5, stack 8A comprises individual slide elements 10A, 10'A temporarily fused together by stripe 40A to allow the stack to be used at a slide element dispensing station 70A without a cartridge as described heretofore. Pusher blade 72A shears off elements 10, 10' and a pusher such as a plunger 60A pushes the stack in the direction of arrow 100. However, unlike the previous embodiment, station 70A is completely open at 102, and plunger 60A is free to be moved away from stack 8A, arrow 104, without causing stack 8A to follow it. Instead, a pair of grippers 110, 112 is used to releasably hold the stack in place. Grippers 110 and 112 each comprise a moment arm 114, a gripping face 116 at one end of the arm, and a hinge pin 118 at the other end of arm 114. A spring such as a torsion spring (not shown), pivots arm 114 outwardly, arrows 120. Gripping face 116 is provided with a surface that specially mates with side edges 20A of stack 8A.

Figure 6:
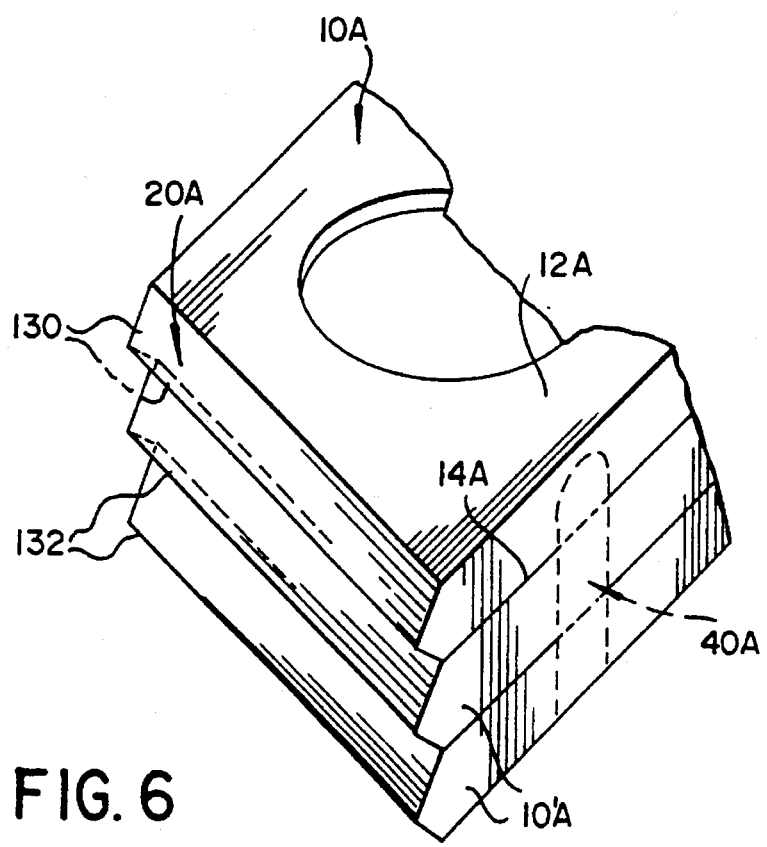
FIG. 6 is an enlarged, fragmentary isometric view of the stack of FIG. 5.

More specifically, FIG. 6, each edge 20A is preferably beveled at 130, to create a gripping lip 132 between the opposite surfaces 12A and 14A. Gripping face 116 is then serrated with grooves that line up with the mating lips 132 of elements 10A and 10'A.

Preferably, the uppermost surface of grippers 110 and 112 is beveled at 132 to provide a camming surface to allow faces 116 to be pushed apart merely by pushing a stack down through opening 102 between grippers 110 and 112.

It is conventional for a bar code to be associated with a stack of slide elements. The code reveals the assay and the lot number, for example. However, this has been done conventionally by imprinting in some way the cartridge surrounding the stack, with such a bar code. In the absence of the cartridge, the question arises as to how to associate the bar code with the stack.

In accordance with the invention, the code is formed on one side face of the stack, e.g., the face comprising side edges 16 of the stack of FIGS. 1 or 2 (edges 16 being hidden in FIG. 2). The code can be imprinted directly via ink jet or laser printing, or it can be printed on a removable label which is temporarily applied to the side face and then removed after the bar code is scanned.

Figure 7:
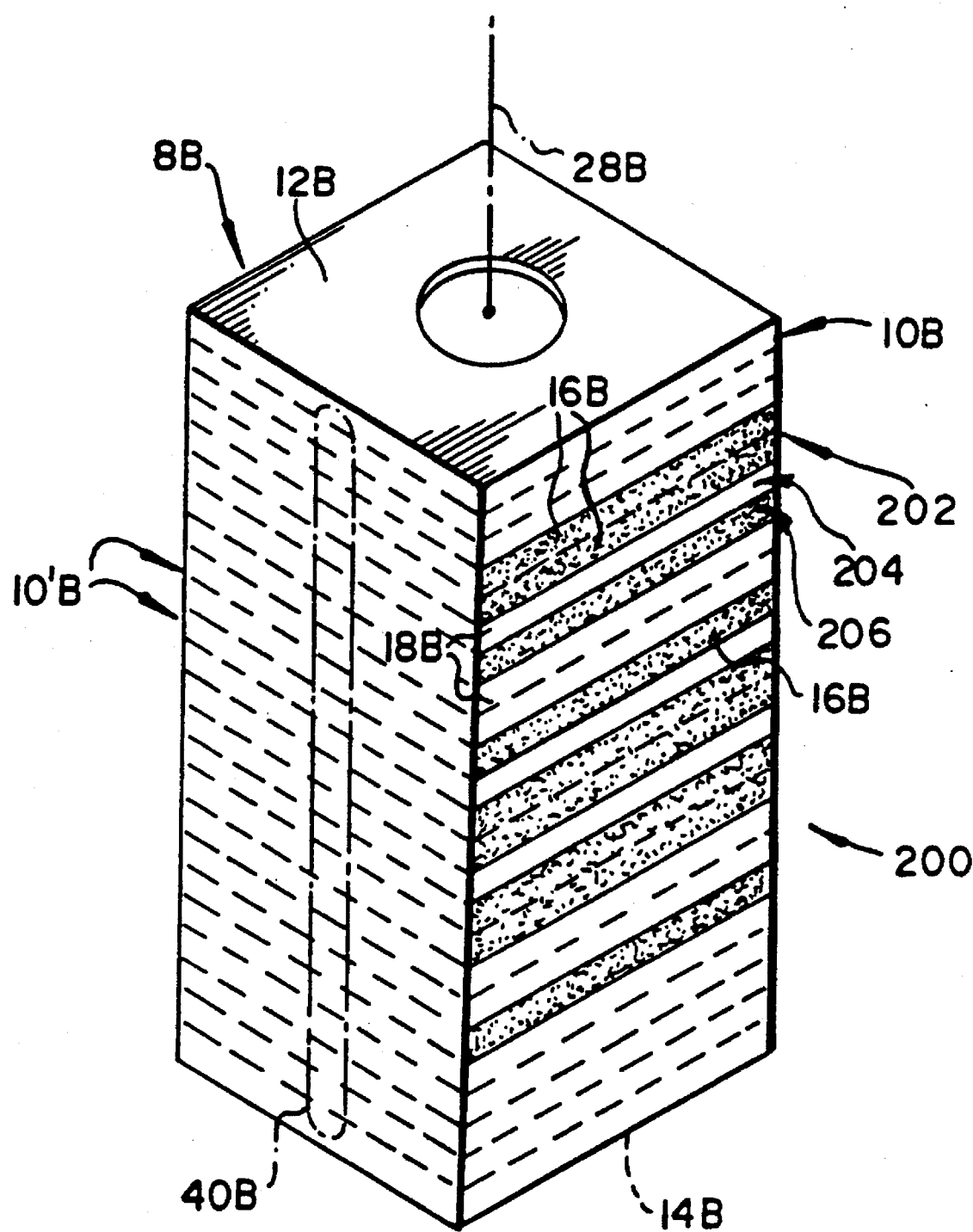
FIG. 7 is a view similar to that of FIG. 2, but illustrating a preferred mode of providing a coding of information on the stack.

In accordance with another aspect of the invention, the bar code can be inherently formed during the stack formation, as an integral part of the stack. Such an embodiment has the advantage that no additional step of ink jet printing or labeling is needed on the stack side face. It is this embodiment that utilizes the colorant in at least one, but not all, side edges, e.g. side edge 16 as described above. It will be readily appreciated that any combination of colored and white (or colorless) side edges in a stack of side edges will, if properly arranged, inherently produce a bar code, FIG. 7. Parts similar to those previously described bear the same reference numeral, to which the distinguishing suffix "B" is appended. Thus, stack 8B comprise elements 10B and 10'B, stacked up with an axis 28B and a temporary stripe 40B, with side edges 16B being blackened for at least part, and preferably all, of that surface. Remaining side edges, e.g. 18B, etc., are white or colorless, as previously described. By having two black side edges 16B adjacent to each other, adjacent to a single white edge 18B, adjacent to a single black edge 16B, etc., the result is a double black bar 202, a single white "blank" 204, and a single black bar 206, etc., of a total bar code 200. All that is needed to create this code is, to pre-arrange each element 10B, 10'B in the stack so as to face outwardly (towards arrow 200), either side edge 16B or side edge 18B, as needed for the code. The code in turn depends on, e.g., the assay type and lot number for that particular stack, which is information readily storable in computer memory of the machine used to stripe the stack, shown in FIG. 4. That is, such machine simply rotates each element about axis 28B until the proper side edge faces "outwardly", FIG. 7, before the striping process begins.

It will be readily appreciated that for this embodiment of the invention, the articles of the stack have a symmetry such that the stack looks the same, except for the color of the side edges, whether edge 16B or 18B faces outwardly against arrow 200. Rectangular or square major surfaces 12B and 14B are most preferred for such symmetry.

The stack 8B of plastic articles so produced has its bar code 200 inherently produced, to indicate, e.g., the type of slide elements present, e.g., those suitable for testing for blood urea nitrogen (BUN). For other kinds of plastic articles not used in diagnostic analyzers, the code can be used to indicate price, date of manufacture, or the like.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. A stack of slide-like test elements assembled together, said stack comprising heat-fusible plastic frames of generally planar configuration, disposed in the stack one above another, the stack having at least one side face, means for temporarily holding said frames together, along at least a common side edge of said frames, and a bar-code extending along said at least one side face of said stack, said bar-code comprising colored bars and white spaces that extend generally parallel to said planar configuration of said frames, said white spaces comprising a white side edge of at least one of said frames that has another side edge not aligned with said one stack side, that is at least partially colored, so that said colored bar or said white space of said bar-code is determined by rotating each slide element about a center point to place either said colored side edge or a white side edge at said one stack side face.

2. A stack as defined in claim 1, wherein said colored bars extend across at least a portion of a side edge of at least one of said frames and are formed by a colorant embedded within said side edge.

3. A stack as defined in claim 1, wherein said stack has an axis of symmetry, and wherein each of said test elements of said stack lies generally in a plane that is generally perpendicular to said axis, so that the uppermost test element of said stack is directly above the lowermost test element.

4. A temporary stack of plastic articles individually releasable from the stack, and bearing bar coded information, the stack comprising a plurality of individual articles each comprising at least two exposable side edges, one of said edges having an exposed colorant in at least a portion of its surface and the other of said edges being substantially free of colorant, said articles being temporarily fused to each other so that said one side edges bearing said exposed colorant are placed in the stack with said other, colorless side edges so as to inherently form said bar-coded information by said colored edges alternating with said colorless edges in the sequence of said coded information.

* * * * *